(12) United States Patent
Doherty, Jr. et al.

(10) Patent No.: US 6,548,490 B1
(45) Date of Patent: *Apr. 15, 2003

(54) TRANSMUCOSAL ADMINISTRATION OF PHOSPHODIESTERASE INHIBITORS FOR THE TREATMENT OF ERECTILE DYSFUNCTION

(75) Inventors: Paul C. Doherty, Jr., Cupertino, CA (US); Virgil A. Place, Kawaihae, HI (US); William L. Smith, Mahwah, NJ (US)

(73) Assignee: Vivus, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/467,094

(22) Filed: Dec. 10, 1999

Related U.S. Application Data

(63) Continuation-in-part of application No. 09/181,070, filed on Oct. 27, 1998, now Pat. No. 6,037,346, which is a continuation-in-part of application No. 08/958,816, filed on Oct. 28, 1997, now abandoned.

(51) Int. Cl.$^7$ .............................................. A61K 31/56

(52) U.S. Cl. ........................................ 514/182; 514/258

(58) Field of Search ................................... 514/182, 258

(56) References Cited

U.S. PATENT DOCUMENTS

| | | |
|---|---|---|
| 3,819,631 A | 6/1974 | Broughton et al. |
| 3,933,822 A | 1/1976 | Broughton et al. |
| 4,039,544 A | 8/1977 | Broughton et al. |
| 4,572,832 A | 2/1986 | Kigasawa et al. |
| 4,666,908 A | 5/1987 | Hamilton |
| 4,764,378 A | 8/1988 | Keith et al. |
| 4,801,587 A | 1/1989 | Voss et al. |
| 5,122,384 A | 6/1992 | Paradissis et al. |
| 5,145,852 A | 9/1992 | Virag |
| 5,242,391 A | 9/1993 | Place et al. |
| 5,250,534 A | 10/1993 | Bell et al. |
| 5,272,147 A | 12/1993 | Bell et al. |
| 5,346,901 A | 9/1994 | Bell et al. |
| 5,407,927 A | 4/1995 | Morales et al. |
| 5,426,107 A | 6/1995 | Bell et al. |
| 5,506,347 A | 4/1996 | Erion et al. |
| 5,565,466 A | 10/1996 | Gioco et al. |
| 5,849,322 A | 12/1998 | Ebert et al. |
| 5,855,905 A | 1/1999 | Oettel et al. |
| 5,898,038 A | 4/1999 | Yallampalli et al. |
| 5,900,247 A | 5/1999 | Rault et al. |
| 5,906,987 A | 5/1999 | Chwalisz et al. |
| 6,191,139 B1 | 2/2001 | Gutterer |
| 6,200,591 B1 | 3/2001 | Hussain et al. |

FOREIGN PATENT DOCUMENTS

| | | |
|---|---|---|
| DE | 4338948 | 5/1995 |
| DE | 19603321 | 8/1997 |
| EP | 0911333 | 4/1999 |
| EP | 0934933 | 8/1999 |
| EP | 0951908 | 10/1999 |
| WO | WO 94/28902 | 12/1994 |
| WO | WO 96/16644 | 6/1996 |
| WO | WO 96/32003 | 10/1996 |
| WO | WO 99/21558 | 5/1999 |
| WO | WO 99/21562 | 5/1999 |
| WO | WO 99/22731 | 5/1999 |
| WO | WO 99/47505 | 9/1999 |
| WO | WO 99/56666 | 11/1999 |
| WO | WO 99/66933 | 12/1999 |
| WO | WO 00/07597 | 2/2000 |
| WO | WO 00/11002 | 3/2000 |
| WO | WO 00/14088 | 3/2000 |
| WO | WO 00/42992 | 7/2000 |
| WO | WO 00/43392 | 7/2000 |
| WO | WO 00/53148 | 9/2000 |
| WO | WO 00/56719 | 9/2000 |
| WO | WO 00/63170 | 10/2000 |

OTHER PUBLICATIONS

Bush et al. (1992), "Nitric Oxide is a Potent Relaxant of Human and Rabbit Corpus Cavernosum," *The Journal of Urology* 147:1650–1655.

Doherty (1997), "Oral, Transdermal, and Transurethral Therapies for Erectile Dysfunction," *Male Infertility and Dysfunction*, Springer–Verlag New York, Inc., pp. 452–467.

Rajfer et al. (1992), "Nitric Oxide as a Mediator of Relaxation of the Corpus Cavernosum in Response to Nonadrenergic, Noncholinergic Neurotransmission," *The New England Journal of Medicine* 326(2):90–94.

Taher et al. (1992), "Cyclic Nucleotide Phosphodiesterase Activity in Human Cavernous Smooth Muscle and the Effect of Various Selective Inhibitors," *International Journal of Impotence Research, Basic and Clinical Studies* 4(2):11.

Trigo–Rocha et al. (1993), "The Role of Cyclic Adenosine Monophosphate, Cyclic Guanosine Monophosphate, Endothelium and Nonadrenergic, Noncholinergic Neurotransmission in Canine Penile Erection," *The Journal of Urology* 149:872–877.

Barnette et al. (1996), "Phosphodiesterase 4: Biological Underpinnings for the Design of Improved Inhibitors," *Pharmacology Reviews and Communications* 8:65–73.

Bivalacqua et al. (1999), "Potentiation of Erectile Response and cAMP Accumulation by Combination of Prostaglandin $E_1$ and Rolipram, a Selective Inhibitor of the Type 4 Phosphodiesterase (PDE 4)," *The Journal of Urology* 162:1–8.

(List continued on next page.)

Primary Examiner—James H. Reamer
(74) *Attorney, Agent, or Firm*—Dianne E. Reed; Reed & Associates

(57) ABSTRACT

A method is provided for treating erectile dysfunction in a mammalian male individual. The method involves the transmucosal administration of a phosphodiesterase inhibitor or a pharmaceutically acceptable salt, ester, amide or derivative thereof, within the context of an effective dosing regimen. Preferred modes of administration include transbuccal, sublingual and transrectal routes. Pharmaceutical formulations and kits are provided as well.

51 Claims, No Drawings

OTHER PUBLICATIONS

Boolell et al. (1996), "Sildenafil: An Orally Active Type 5 Cyclic GMP–Specific Phosphodiesterase Inhibitor for the Treatment of Penil Erectile Dysfunction," *International Journal of Impotence Research* 8:47–52.

Burnouf et al. (1998), "Phosphodiesterases 4 Inhibitors," *Annual Reports In Medicinal Chemistry* 33:91–109.

Christensen et al. (1996), "Molecular Aspects of Inhibitor Interaction with PDE4," *Phosphodiesterase Inhibitors*, Academic Press, Harcourt Brace and Company, Publishers, pp. 185–207.

Degerman et al. (1996), "cGMP–Inhibited Phosphodiesterases (PDE3 Gene Family)," *Biochemical Society Transactions* 24(4):1010–1014.

Degerman et al. (1998), "Phosphorylation and Activation of Hormone–Sensitive Adiposyte Phosphodiesterase Type 3B," *Methods: A companion to Methods in Enzymology* 14:43–53.

Doherty (1999), "Phosphodiesterase 4 Inhibitors as Novel Anti–Inflammatory Agents," *Current Opin. Chem. Brol.* 3(4):466–473.

Komas et al. (1996), "c.GMP–Inhibited Phosphodiesterases (PDE3)," *Phosphodiesterase Inhibitors*, Academic Press, Harcourt Brace and Company, Publishers, pp. 89–109.

Martinez–Piñeiro et al. (1993), "Cyclic Guanosine Monophosphate Mediates Penile Erection in the Rat," *European Urology* 24:492–499.

McGarry et al. (1999), "Benzofuran Based PDE4 Inhibitors," *Biorganic & Medicinal Chemistry* 7:1131–1139.

Müller et al. (1996), "Subtypes of the Type 4 cAMP Phosphodiesterases: Structure, Regulation and Selective Inhibition," *Trends Pharm. Sci.* 17(8):294–298.

Perrier et al. (1999), "Substituted Furans as Inhibitors of the PDE4 Enzyme," *Bioorganic & Medicinal Chemistry Letters* 9:323–326.

Polson et al. (1996), "Cyclic Nucleotide Phosphodiesterases and Vascular Smooth Muscle," *Annu. Rev. Pharmacol. Toxicol.* 36:403–427.

Shimizu et al. (1999), "OPC–13013, A Cyclic Nucleotide Phosphodiesterase Type III Inhibitor, Inhibits Cell Proliferation and Transdifferentiation of Cultured Rat Hepatic Stellate Cells," *Life Sciences* 64(23):2081–2088.

Sparwasser et al. (1994), "Smooth Muscle Tone Regulation in Rabbit Cavernosal and Spongiosal Tissue by Cyclic AMP– and Cyclic GMP–Dependent Mechanisms," *The Journal of Urology* 152:2159–2163.

Stief et al. (1995), "Cyclic Nucleotide Phosphodiesterase (PDE) Isoenzymes in Human Cavernous Smooth Muscle: Characterization and Functional Effects of PDE–Inhibitors In Vitro and In Vivo," *International Journal of Impotence Research, Basic and Clinical Studies* 78(1):6–7.

Suzumura et al. (1999), "Ibudilast Suppresses TNAα Productioin By Glial Cells Functioning Mainly as Type III Phosphodiesterase Inhibitor in the CNS," *Brain Research* 837:203–212.

Taher et al. (1997), "Cyclic Nucleotide Phosphodiesterase in Human Cavernous Smooth Muscle," *World Journal of Urology* 15:32–35.

Truss et al. (1998), "Phosphodiesterase Inhibitors in the Treatment of Erectile Dysfunction," *Drugs of Today* 34(9), summary only.

TRANSMUCOSAL ADMINISTRATION OF PHOSPHODIESTERASE INHIBITORS FOR THE TREATMENT OF ERECTILE DYSFUNCTION

CROSS-REFERENCE TO RELATED APPLICATIONS

This application is a continuation-in-part of U.S. Ser. No. 09/181,070, filed Oct. 27, 1998 now U.S. Pat. No. 6,037, 346, which is a continuation-in-part of U.S. Ser. No. 08/958, 816, filed Oct. 28, 1997 now abandoned, the disclosures of which are hereby incorporated by reference.

TECHNICAL FIELD

This invention relates generally to methods and pharmaceutical compositions for treating erectile dysfunction; more particularly, the invention relates to transmucosal (e.g., buccal, sublingual and transrectal), administration of phosphodiesterase inhibitors to treat erectile dysfunction.

BACKGROUND

Impotence is the consistent inability to achieve or sustain an erection of sufficient rigidity for sexual intercourse. It has recently been estimated that approximately 10 million American men are impotent (R. Shabsigh et al., "Evaluation of Erectile Impotence," Urology 32:83–90 (1988); W. L. Furlow, "Prevalence of Impotence in the United States," *Med. Aspects Hum. Sex.* 19:13-6 (1985)). Impotence is recognized to be an age-dependent disorder, with an incidence of 1.9 percent at 40 years of age and 25 percent at 65 years of age (A. C. Kinsey et al., "Age and Sexual Outlet," in *Sexual Behavior in the Human Male*; A. C. Kinsey et al., eds., Philadelphia, Pa.: W. B. Saunders, 218–262 (1948)). In 1985 in the United States, impotence accounted for more than several hundred thousand outpatient visits to physicians (National Center for Health Statistics, National Hospital Discharge Survey, 1985, Bethesda, Md., Department of Health and Human Services, 1989 DHHS publication no. 87–1751). Depending on the nature and cause of the problem, treatments include psychosexual therapy, hormonal therapy, administration of vasodilators such as nitroglycerin and α-adrenergic blocking agents ("α-blockers"), oral administration of other pharmaceutical agents, vascular surgery, implanted penile prostheses, vacuum constriction devices and external aids such as penile splints to support the penis or penile constricting rings to alter the flow of blood through the penis.

A number of causes of impotence have been identified, including vasculogenic, neurogenic, endocrinologic and psychogenic. Vasculogenic impotence, which is caused by alterations in the flow of blood to and from the penis, is thought to be the most frequent organic cause of impotence. Common risk factors for vasculogenic impotence include hypertension, diabetes, cigarette smoking, pelvic trauma, and the like. Neurogenic impotence is associated with spinal-cord injury, multiple sclerosis, peripheral neuropathy caused by diabetes or alcoholism and severance of the autonomic nerve supply to the penis consequent to prostate surgery. Erectile dysfunction is also associated with disturbances in endocrine function resulting in low circulating testosterone levels and elevated prolactin levels.

Impotence can also be a side effect of various classes of drugs, in particular, those that interfere with central neuroendocrine control or local neurovascular control of penile smooth muscle. Krane et al., *New England Journal of Medicine* 32:1648 (1989). Penile erection requires (1) dilation of the arteries that regulate blood flow to the lacunae of the corpora cavemosum, (2) relaxation of trabecular smooth muscle, which facilitates engorgement of the penis with blood, and (3) compression of the venules by the expanding trabecular walls to decrease venous outflow.

Trabecular smooth muscle tone is controlled locally by adrenergic (constrictor), cholinergic (dilator) and nonadrenergic, noncholinergic (dilator) innervation, and by endothelium-derived vasoactive substances such as vasoactive intestinal polypeptide (VIP), prostanoids, endothelin and nitric oxide. High sympathetic tone (noradrenergic) is implicated in erectile dysfunction, and, in some patients, the disorder can be successfully treated with noradrenergic receptor antagonists. See, e.g., Krane et al., supra.

There is also evidence that dopaminergic mechanisms are involved in erectile function. For example, pharmacologic agents that elevate the level of brain dopamine or stimulate brain dopamine receptors increase sexual activity in animals (see, e.g., Gessa & Tagliamonte, *Life Sciences* 14:425 (1974); Da Prada et al., *Brain Research* 57:383 (1973)).

Administration of L-DOPA, a dopamine precursor, enhances sexual activity in male rats. L-DOPA has been used in the treatment of Parkinsonism and is known to act as an aphrodisiac in some patients (Gessa & Tagliamonte, supra; Hyppa et al., *Acta Neurologic Scand*. 46:223 (Supp. 43, 1970)). Specific dopamine agonists have been studied for their effects on erectile function. Apomorphine, (n-propyl) norapo-morphine, bromocryptine, amantidine, fenfluramine, L-DOPA and various other pharmacological activators of central dopaminergic receptors have been found to increase episodes of penile erection in male rats (Benassi-Benelli et al., *Arch. int. Pharmacodyn*. 242:241 (1979); Poggioli et al., *Riv. di Farm. & Terap*. 9:213 (1978); Falaschi et al., *Apomorphine and Other Dopaminomimetics*, 1:117–121 (Gessa & Corsini, Eds., Raven Press, N.Y.)). In addition, U.S. Pat. No. 4,521,421 to Foreman relates to the oral or intravenous administration of quinoline compounds to treat sexual dysfunction in mammals.

The currently available dopamine agonists, with few exceptions, have found limited use in the treatment of erectile dysfunction because of their peripheral side effects. These effects include nausea and vomiting, postural hypotension, arrhythmias, tachycardia, dysphoria, psychosis, hallucinations, drowsiness and dyskinesias (See, e.g., Martindale *The Extra Pharmacopoeia*, 31st Ed., pages 1151–1168).

The invention described herein provides a means to avoid the above-mentioned problems encountered with previously known methods for treating erectile dysfunction. Specifically, the invention relates to methods and formulations for effectively treating erectile dysfunction by transmucosally, e.g., buccally, sublingually or transrectally, administering a selected active agent, wherein the active agent is an inhibitor of a phosphodiesterase.

Phosphodiesterases are a class of intracellular enzymes involved in the metabolism of the second messenger nucleotides, cyclic adenosine monophosphate (cAMP), and cyclic guanosine monophosphate (cGMP) (see, e.g., Doherty, "Oral, Transdermal, and Transurethral Therapies for Erectile Dysfunction" in *Male Infertility and Dysfunction*, Helistrom, ed., Chapter 34 (New York, N.Y.: Springer-VerlagHellstrom, 1997)). Numerous phosphodiesterase inhibitors have previously been described in the literature for a variety of therapeutic uses, including treatment of obstructive lung disease, allergies, hypertension, angina, congestive heart failure and depression (see, e.g., Goodman and Gilman's *The Pharmacological Basis of Therapeutics* Ninth Edition, Chapter 34). Oral and parenteral administration of phosphodiesterase inhibitors, as alluded to above, have also been suggested for the treatment of erectile dysfunction (Doherty, supra; see also PCT Publication Nos. WO 96/16644, and WO 94/28902). The phosphodiesterases have been classified into seven major families, Types I–VII, based on amino acid or DNA sequences. The members of the family vary in their tissue, cellular and subcellular distribution, as well as their links to cAMP and cGMP pathways. For example, the corpora cavernosa contains: Type III phosphodiesterases, which are cAMP-specific cGMP inhibitable; Type IV phosphodiesterases, the high affinity, high-specificity cAMP-specific form; and Type V phosphodiesterases, one of the cGMP-specific forms.

The invention, as noted above, is directed to transmucosal administration of pharmacologically active agents to treat erectile dysfunction. The agents are preferably, although not necessarily, Type III, Type IV or Type V phosphodiesterase inhibitors. Surprisingly, it has now been found by the inventors herein that transmucosal and particularly buccal, sublingual or transrectal administration of these phosphodiesterase inhibitors as disclosed herein is highly effective in treating erectile dysfunction, including vasculogenic impotence. Transmucosal and particularly buccal, sublingual or transrectal administration of phosphodiesterase inhibitors to treat erectile dysfunction accordingly represents an important advance in the treatment of impotence and other erectile disorders.

SUMMARY OF THE INVENTION

It is a primary object of the invention to address the above-described need in the art by providing a novel method for treating erectile dysfunction by transmucosally administering an effective amount of a selected phosphodiesterase inhibitor to an individual in need of such therapy.

It is another object of the invention to provide such a method wherein the phosphodiesterase inhibitor is administered buccally.

It is an additional object of the invention to provide such a method wherein the phosphodiesterase inhibitor is administered sublingually.

It is still another object of the invention to provide such a method wherein the phosphodiesterase inhibitor is administered transrectally.

It is a further object of the invention to provide pharmaceutical formulations for carrying out the aforementioned methods.

It is yet another object of the invention to provide a kit capable of use by an individual for self-administration of a phosphodiesterase inhibitor as provided herein.

Additional objects, advantages and novel features of the invention will be set forth in part in the description that follows, and in part will become apparent to those skilled in the art upon examination of the following, or may be learned by practice of the invention.

In a first aspect of the invention, a method is provided for treating an individual prone to erectile dysfunction, e.g., vasculogenic erectile dysfunction, the method comprising transmucosally administering to the individual a pharmaceutical formulation containing a phosphodiesterase inhibitor. Administration of the pharmaceutical formulation is carried out within the context of a predetermined dosing regimen such that the agent is effective in the treatment of erectile dysfunction. The method is especially useful in the treatment of vasculogenic impotence, although other types of erectile dysfunction may also be treated using the present formulations, e.g., neurogenic, endocrinologic and psychogenic impotence. Drug delivery is preferably effected through the buccal mucosa, sublingual mucosa or transrectal mucosa but the drug may also be administered through other mucosal surfaces of the body. For buccal administration, the active agent is typically although not necessarily administered by affixing a buccal dosage unit to the buccal mucosa of the individual undergoing treatment, and allowing the dosage unit to remain in place until drug delivery is complete. Alternatively, buccal administration may be effected by the application to the buccal mucosa of a cream, ointment or paste containing the active agent. For sublingual administration, the active agent is typically although not necessarily administered by placing a sublingual tablet under the tongue of the individual undergoing treatment, and allowing the tablet to remain in place until tablet disintegration and thus drug delivery is complete. For transrectal administration, the active agent is typically although not necessarily administered by placing a suppository within the rectum and allowing the dosage unit to remain in place until melting of the carrier and thus drug delivery is complete. Alternatively, transrectal administration may be effected using a cream, ointment or solution (e.g., enema) containing the active agent.

In another aspect of the invention, a pharmaceutical formulation is provided for carrying out the present method for treating erectile dysfunction. The pharmaceutical formulation comprises an effective amount of a phosphodiesterase inhibitor, a carrier or vehicle suited to transmucosal administration and, optionally, a permeation enhancer. The formulation may contain one or more additional active agents, e.g., dopaminergic drugs, smooth muscle relaxants, vasoactive drugs, and additives, e.g., excipients, surfactants, preservatives (e.g., antioxidants), stabilizers, chelating agents, enzyme inhibitors, antibacterial agents, binders, diluents, lubricants, and the like, as will be appreciated by those skilled in the art of drug formulation preparation and delivery. Buccal formulations will generally although not necessarily comprise a solid dosage unit containing the active agent, a hydrolyzable (or "bioerodible") polymeric carrier, and a means for affixing the dosage unit to the buccal mucosa. The latter may represent a separate adhesive component in the formulation, or the polymeric carrier itself may serve as an adhesive. Sublingual formulations comprise a dosage form for application to the sublingual mucosa and a carrier suitable for sublingual drug delivery. Thus, sublingual formulations will generally although not necessarily comprise a solid dosage unit containing the active agent and one or more vehicles and a lubricant. Transrectal formulations comprise a dosage form for application to the rectal mucosa and a carrier suitable for transrectal drug delivery. Thus, transrectal formulations in the form of a suppository will generally although not necessarily comprise a solid dosage unit containing the active agent and one or more suppository bases.

In another aspect, a kit is provided to assist an individual in drug administration to carry out the method of the invention. Generally, the kit will include the following components: a pharmaceutical formulation comprising the phosphodiesterase inhibitor to be administered; a container housing the pharmaceutical formulation during storage and prior to use; and instructions for carrying out drug administration in a manner effective to treat erectile dysfunction.

When the kit is for assisting an individual in buccal drug administration, specifically, the kit will include at least the following: a buccal dosage unit comprising the active agent and a bioerodible polymeric carrier; a container housing the dosage unit prior to use; and written instructions for carrying out administration of the active agent for the intended therapeutic purpose.

DETAILED DESCRIPTION OF THE INVENTION

DEFINITIONS:

Before describing the present invention in detail, it is to be understood that this invention is not limited to particular drugs or drug delivery systems, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, reference to "a phosphodiesterase inhibitor" includes a mixture of two or more such compounds, reference to "a permeation enhancer" includes mixtures of two or more enhancers, and the like.

In describing and claiming the present invention, the following terminology will be used in accordance with the definitions set out below.

The term "erectile dysfunction" is intended to include any and all types of erectile dysfunction, including: vasculogenic, neurogenic, endocrinologic and psychogenic impotence ("impotence" is used here in its broadest sense to indicate a periodic or consistent inability to achieve or sustain an erection of sufficient rigidity for sexual intercourse; see U.S. Pat. No. 5,242,391 to Place et al., cited supra); Peyronie's syndrome; priapism; premature ejaculation; and any other condition, disease or disorder, regardless of cause or origin, which interferes with at least one of the three phases of human sexual response, i.e., desire, excitement and orgasm (see Kaplan, *Disorders of Sexual Desire* (New York, N.Y.: Brunner Mazel Book Inc., 1979)).

The terms "treating" and "treatment" as used herein refer to reduction in severity and/or frequency of symptoms, elimination of symptoms and/or underlying cause, prevention of the occurrence of symptoms and/or their underlying cause, and improvement or remediaton of damage. The present method of "treating" erectile dysfunction, as the term is used herein, thus encompasses both prevention of the disorder in a predisposed individual and treatment of the disorder in a clinically symptomatic individual.

The term "phosphodiesterase inhibitor" as used herein is intended to mean an agent that is capable of inhibiting or selectively reducing the activity of any one or more phosphodiesterases.

The terms "active agent," "drug" and "pharmacologically active agent" are used interchangeably herein to refer to a chemical material or compound that induces a desired effect. In the preferred embodiment herein, the terms refer to a phosphodiesterase inhibitor which is capable of being delivered transmucosally. Included are derivatives and analogs of those compounds or classes of compounds specifically mentioned which also induce the desired effect.

"Penetration enhancement" or "permeation enhancement" as used herein relates to an increase in the permeability of the mucosal tissue to the selected pharmacologically active agent, i.e., so that the rate at which the drug permeates therethrough is increased.

"Carriers" or "vehicles" as used herein refer to carrier materials suitable for transmucosal drug administration. Carriers and vehicles useful herein include any such materials known in the art which is nontoxic and does not interact with other components of the composition in a deleterious manner.

By "transmucosal" drug delivery is meant administration of a drug to the mucosal surface of an individual so that the drug passes through the mucosal tissue and into the individual's blood stream. A preferred form of transmucosal drug delivery herein is "buccal" or "transbuccal" drug delivery which refer to delivery of a drug by passage of a drug through an individual's buccal mucosa and into the bloodstream. Another preferred from of transmucosal drug delivery herein is "sublingual" or "transublingual" drug delivery which refer to delivery of a drug by passage of a drug through an individual's sublingual mucosa and into the bloodstream. An additional preferred form of transmucosal drug delivery herein is "rectal" or "transrectal" drug delivery which refer to delivery of a drug by passage of a drug through an individual's rectal mucosa and into the bloodstream.

By an "effective" amount of a drug or pharmacologically active agent is meant a nontoxic but sufficient amount of the drug or agent to provide the desired effect, i.e., treatment of erectile dysfunction.

ACTIVE AGENTS FOR TREATMENT OF ERECTILE DYSFUNCTION:

In order to carry out the method of the invention, a selected phosphodiesterase inhibitor is administered transmucosally to an individual prone to erectile dysfunction.

The active agent herein may be any agent which is effective to inhibit the activity of a phosphodiesterase. Suitable phosphodiesterase inhibitors include, but are not limited to, inhibitors of the Type III phosphodiesterases (the cAMP-specific-cGMP inhibitable form), the Type IV phosphodiesterase (the high affinity-high specificity cAMP form) and the Type V phosphodiesterases (the cGMP specific form). Additional inhibitors that may be used in conjunction with the present invention are cGMP-specific phosphodiesterase inhibitors other than Type V inhibitors.

Examples of Type III phosphodiesterase inhibitors that may be administered herein include, but are not limited to, bipyridines such as milrinone and amrinone; imidazolones such as piroximone and enoximone; imidazolines such as imazodan and 5-methyl-imazodan; dihydropyridazinones such as indolidan and LY181512

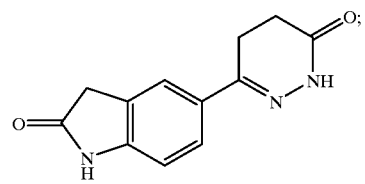

LY 181512 dihydroquinolinone compounds such as cilostamide, cilostazol, vesnarinone and OPC 3911

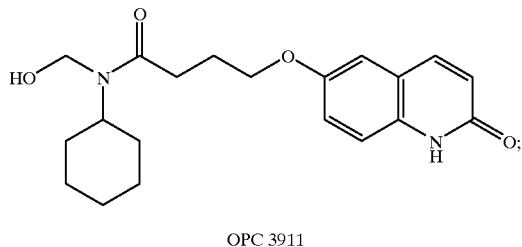

OPC 3911 other compounds such as anagrelide, bemoradan, ibudilast, isomazole, lixazinone, motapizone, olprinone, phthalazinol, pimobendan, quazinone, siguazodan and trequinsin; and mixed Type III and Type IV inhibitors such as benafentrine, cis-6-[p-acetamidophenyl]- 1,2,3,4,4a,10b-hexahydro-8, 9-dimethoxy-2-methylbenzo-[c][1,6]-naphthyridine, EMD 54622 (5-[1-(3,4-dimethoxybenzoyl)-4,4-dimethyl-1, 2,3,4-tetrahydrochinolin-6-yl]-6-methyl-3,6-dihydro-1,3, 4-thiadiazin-2-one), Org 20241 (N-hydroxy-4-[3,4-dimethoxyphenyl]-thiazole-2-carboximidamide), Org30029 (N-hydroxy-5,6-dimethoxybenzo-[b]-thiophene-2-carboximidamide), saterinone, tolafentrine and zardaverine. Preferred Type III PDE inhibitors herein are bipyridines, imidazolones, imidazolines, dihydropyridazinones and dihydroquinolinone compounds. Of these, the inhibitors that are particularly preferred herein arc milrinone, amrinone, piroximone, enoximone, imazodan, 5-methyl-imazodan, indolidan, cilostamide, cilostazol and vesnarinone. The inhibitors may be used alone or in combination; if in combination, they may be administered either simultaneously or sequentially.

Examples of Type IV phosphodiesterase inhibitors that may be administered herein include, but are not limited to: pyrrolidinones such as rolipram (4-(3-cyclopentyloxy-4'-methoxyphenyl)-2-pyrrolidinone)) and rolipram derivatives such as RO20-1724 (4-(3-butyloxy-4-methoxyphenyl)-imidazolidinone) and RS 33793 (8-(3-nitrophenyl)-6-(3-methyl-2-butenyl)pyrido[2,3a]pyrazin-5-one); quinazolinediones such as nitraquazone (3-[3'-nitrophenyl] N-ethylquinazoline-2, 6-dione), CP-77059 (1-(carbomethoxyphenyl)-3-benzylpyrido[2,3d] pyrimidine-2, 4(1H,3H)dione), RS-25344 (1-(3-nitrophenyl)-3-(4-pyridylmethyl)-1,2,3,4-tetrahydro pyrido(2,3-d) pyrimidine-2,4-dione)) and other nitraquazone analogs; xanthine derivatives such as denbufylline (1,3-di-n-butyl-7-[2'-oxopropyl] xanthine), XT-44 (1-n-butyl-3-n-propylxanthine), arofylline (LAS 31025; 1-propyl-3-(4-chlorophenyl)-xanthine) and BRL 61063

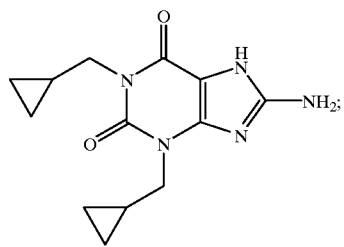

BRL 61063 phenyl ethyl pyridines such as CDP 840 (4-(1-(3-cyclopentyloxy-4-methoxyphenyl)-2-phenylethyl) pyridine)

and compounds disclosed in WO 97/22585 to Guay et al.; tetrahydropyrimidones such as atizoram (CP 80633)

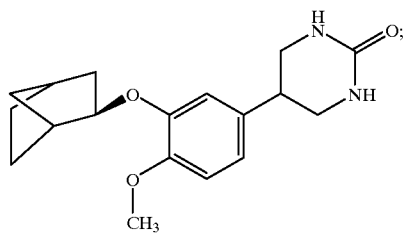

CP 80633 diazepine derivatives such as CI 1018

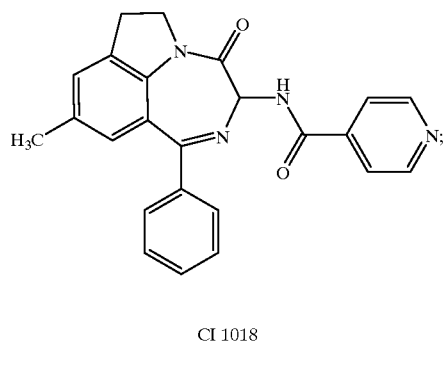

CI 1018 and compounds disclosed in WO 97/36905 to Pascal et al.; oxime carbamates such as filaminast (PDA-641); naphthyridinones such as RS 17597

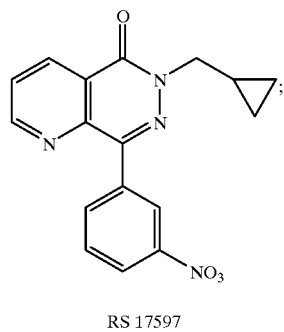

RS 17597 benzofurans such as 2-butyl-7-methoxy-benzofuran-4-carboxylic acid (3,5-dichloro-pyridin-4yl)-amide, 2-benzyl-7-methoxy-benzofuran-4-carboxylic acid (3,5-dichloro-pyridin-4-yl)-amide, 7-methoxy-2-phenethyl-benzofuran-4-carboxylic acid (3,5-dichloropyridin-4-yl)-amide and 5-(2-butyl-7-methoxy-benzofuran-4-yl)-tetrahydro-pyrimidin-2-one, phenyldihydrobenzofurane compounds such as those disclosed in U.S. Pat. No. 5,902,824; 4-substituted benzofurane compounds such as those disclosed in EP 819688A1; substituted furans as disclosed in Perrier et al. Bioorg. Med. Chem. Lett. 9:323–326 (1999); naphthalene derivatives such as T 440

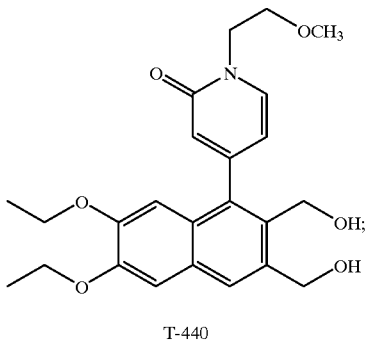

T-440 purine derivatives such as V-112294A

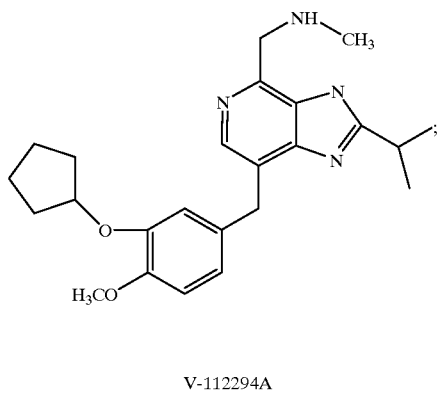

V-112294A cyclohexane carboxylic acids such as ariflo (SB 207499, (c-4-cyano-4-[3'-cyclopentyloxy-4'-methoxyphenyl]-r-1-cyclohexanecarboxylic acid)); benzamides such as piclamilast (RP73401; N-(3,5-dichloro-4-pyridyl)-3-cyclopentoxy-4-methoxy benzamide); benzothiophenes such as tibenelast (LY 186655); pyridopyridazinones such as

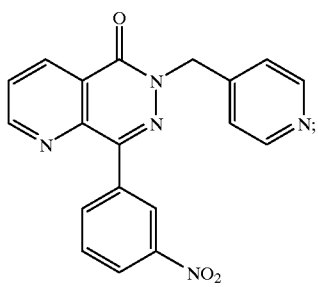

imidazolidinones such as

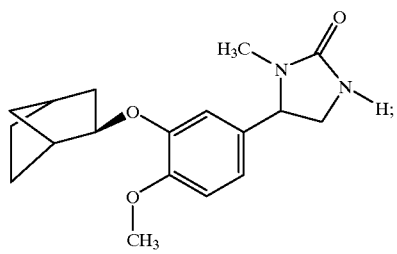

substituted phenyl compounds, as disclosed in U.S. Pat. No. 5,891,896 to Warrellow et al.; substituted biphenyl compounds as disclosed in U.S. Pat. No. 5,877,190 to Dhainaut et al.; etazolate; and S-(+)-glaucine ((S)-(+)-1,2,9,10-tetramethoxyaporphine).

Examples of Type V phosphodiesterase inhibitors include, but are not limited to, zaprinast, MY5445, dipyridamole, and sildenafil. Other Type V phosphodiesterase inhibitors are disclosed in PCT Publication Nos. WO 94/28902 and WO 96/16644.

The compounds described in PCT Publication No. WO 94/28902 are pyrazolopyrimidinones. Examples of the inhibitor compounds include 5-(2-ethoxy-5-morpholinoacetylphenyl)-1-methyl-3-n-propyl-1,6-dihydro-7H-pyrazolo[4,3-d]pyrimidin-7-one, 5-(5-morpholinoacetyl-2-n-propoxyphenyl)-1-methyl-3-n-propyl-1,6-dihydro-7H-pyrazolo[4,3-d]pyrimidin-7-one, 5-[2-ethoxy-5-(4-methyl-1-piperazinylsulfonyl)-phenyl]-1-methyl-3-n-propyl-1,6-dihydro-7H-pyrazolo[4,3-d] pyrimidin-7-one, 5-[2-allyloxy-5-(4-methyl-1-piperazinylsulfonyl)-phenyl]-1-methyl-3-n-propyl-1,6-dihydro-7H-pyrazolo[4,3-d]pyrimidin-7-one, 5-[2-ethoxy-5-[4-(2-propyl)-1-piperazinylsulfonyl)-phenyl]-1-methyl-3-n-propyl-1, 6-dihydro-7H-pyrazolo[4,3-d]pyrimidin-7-one, 5-[2-ethoxy-5-[4-(2-hydroxyethyl)-1-piperazinylsulfonyl) phenyl]-1-methyl-3-n-propyl-1,6-dihydro-7H-pyrazolo[4,3-d]pyrimidin-7-one, 5-[5-[4-(2-hydroxyethyl)-1-piperazinylsulfonyl]-2-n-propoxyphenyl]-1-methyl-3-n-propyl-1,6-dihydro-7H-pyrazolo[4,3-d]pyrimidin-7-one, 5-[2-ethoxy-5-(4-methyl-1-piperazinylcarbonyl)phenyl]-1-methyl-3-n-propyl-1,6-dihydro-7H-pyrazolo[4,3-d] pyrimidin-7-one, and 5-[2-ethoxy-5-(1-methyl-2-imidazolyl)phenyl]-1-methyl-3-n-propyl-1,6-dihydro-7H-pyrazolo[4,3-d]pyrimidin-7-one.

The phosphodiesterase inhibitors described in PCT Publication No. WO 96/16644 include griseolic acid derivatives, 2-phenylpurinone derivatives, phenylpyridone derivatives, fused and condensed pyrimidines, pyrimidopyrimidine derivatives, purine compounds, quinazoline compounds, phenylpyrimidinone derivative, imidazoquinoxalinone derivatives or aza analogues thereof, phenylpyridone derivatives, and others. Specific examples of the phosphodiesterase inhibitors disclosed in WO 96/16644 include 1,3-dimethyl-5-benzylpyrazolo[4,3-d]pyrimidine-7-one, 2-(2-propoxyphenyl)-6-purinone, 6-(2-propoxyphenyl)-1,2-dihydro-2-oxypyridine-3-carboxamide, 2-(2-propoxyphenyl)-pyrido[2,3-d]pyrimid-4(3H)-one, 7-methylthio-4-oxo-2-(2-propoxyphenyl)-3,4-dihydro-pyrimido[4,5-d]pyrimidine, 6-hydroxy-2-(2-propoxyphenyl)pyrimidine-4-carboxamide, 1-ethyl-3-methylimidazo[1,5a]quinoxalin-4(5H)-one, 4-phenylmethylamino-6-chloro-2-(1-imidazoloyl) quinazoline, 5-ethyl-8-[3-(N-cyclohexyl-N-methylcarbamoyl)-propyloxy]-4,5-dihydro-4-oxo-pyrido[3, 2-e]-pyrrolo1,2-a]pyrazine, 5'-methyl-3'-(phenylmethyl)-spiro[cyclopentane-1,7'(8'H)-(3'H)-imidazo[2,1-b]purin]4' (5'H)-one, 1-[6-chloro-4-(3,4-methylenedioxybenzyl)-aminoquinazolin-2-yl)piperidine-4-carboxylic acid, (6R, 9S)-2-(4-trifluoromethyl-phenyl)methyl-5-methyl-3,4,5,6a, 7,8,9,9a-octahydrocyclopent[4,5]-imidazo[2,1-b]-purin-4-one, 1-t-butyl-3-phenylmethyl-6-(4-pyridyl)pyrazolo[3,4-d]-pyrimid-4-one, 1-cyclopentyl-3-methyl-6-(4-pyridyl)-4, 5-dihydro-1H-pyrazolo[3,4-d]pyrimid-4-one, 2-butyl-1-(2-chlorobenzyl)6-ethoxy-carbonylbenzimidazole, and 2-(4-carboxypiperidino)-4-(3,4-methylenedioxy-benzyl)amino-6-nitroquinazoline, and 2-phenyl-8-ethoxycycloheptimidazole.

Still other Type V phosphodiesterase inhibitors useful in conjunction with the present invention include: IC-351 (ICOS); 4-bromo-5-(pyridylmethylamino)-6-[3-(4-chlorophenyl)propoxy]-3 (2H)pyridazinone; 1-[4-[(1,3-benzodioxol-5-ylmethyl)amiono]-6-chloro-2-quinazolinyl]-4-piperidine-carboxylic acid, monosodium salt; (+)-cis-5,6a,7,9,9,9a-hexahydro-2-[4-(trifluoromethyl)-phenylmethyl-5-methyl-cyclopent-4,5]imidazo[2,1-b]purin-4(3H)one; furazlocillin; cis-2-hexyl-5-methyl-3,4,5,6a,7,8,9,9a-octahydrocyclopent[4,5]imidazo[2,1-b]purin-4-one; 3-acetyl-1-(2-chlorobenzyl)-2-propylindole-6-carboxylate; 4-bromo-5-(3-pyridylmethylamino)-6-(3-(4-chlorophenyl)propoxy)-3-(2H)pyridazinone; 1-methyl-5-(5-morpholinoacetyl-2-n-propoxyphenyl)-3-n-propyl-1,6-dihydro-7H-pyrazolo(4,3-d)pyrimidin-7-one; 1-[4-[(1,3-benzodioxol-5-ylmethyl)amino]-6-chloro-2-quinazolinyl]-4-piperidinecarboxylic acid, monosodium salt; pyrrolo[1,2-c]imidazolone derivatives (as described in U.S. Pat. No. 4,937,258 to Shaw); 1-phenylmethyl-N-[[4-ethyl-2-(2-ethyl-4-methyl-1H-imidazol-1-yl)]pyrimidin-5-yl]-1H-imidazol-2-carboxamide; 1-phenylmethyl-N-[4-ethyl-2-(1H-imidazol-1-yl)pyrimidin-5-yl]-1H-imidazol-2-carboxamide (see U.S. Pat. No. 5,318,975 to Lis); 4,9-diethyl-2-(2-ethyl-4-methyl-1H-imidazol-1-yl)-7-methylimidazo[5,1-h]pteridin-6(5H)-one; and 9-ethyl-2(2-ethyl-4-methyl-1H-imidazol-1-yl)-7-methyl-4-(2-propyl) imidazo[5,1-h]pteridin-6(5H)-one (see U.S. Pat. No. 5,602,252 to Davey); Pharmaprojects No. 4516 (Glaxo Wellcome); Pharmaprojects No. 5051 (Bayer); Pharmaprojects No. 5064 (Kyowa Hakko; see WO 96/26940); Pharmaprojects No. 5069 (Schering Plough); GF-196960 (Glaxo Wellcome); and Sch-51866.

Other phosphodiesterase inhibitors that may be co-administered with the Type III PDE inhibitor include nonspecific phosphodiesterase inhibitors such as aminophylline, enprofylline, isbufylline, IBMX, papaverine, pentoxifylline, theobromine and theophylline, and direct vasodilators such as hydralazine.

The active agents may be administered, if desired, in the form of salts, esters, amides, prodrugs, derivatives, and the like, provided the salt, ester, amide, prodrug or derivative is suitable pharmacologically, i.e., effective in the present method. Salts, esters, amides, prodrugs and other derivatives of the active agents may be prepared using standard procedures known to those skilled in the art of synthetic organic chemistry and described, for example, by J. March, *Advanced Organic Chemistry: Reactions, Mechanisms and Structure*, 4th Ed. (New York: Wiley-Interscience, 1992). For example, acid addition salts are prepared from the free base using conventional methodology, and involves reaction with a suitable acid. Generally, the base form of the drug is dissolved in a polar organic solvent such as methanol or ethanol and the acid is added thereto. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Particularly preferred acid addition salts of the active agents herein are halide salts, such as may be prepared using hydrochloric or hydrobromic acids. Conversely, preparation of basic salts of acid moieties which may be present on a phosphodiesterase inhibitor molecule are prepared in a similar manner using a pharmaceutically acceptable base such as sodium hydroxide, potassium hydroxide, ammonium hydroxide, calcium hydroxide, trimethylamine, or the like. Particularly preferred basic salts herein are alkali metal salts, e.g., the sodium salt, and copper salts. Preparation of esters involves functionalization of hydroxyl and/or carboxyl groups which may be present within the molecular structure of the drug. The esters are typically acyl-substituted derivatives of free alcohol groups, i.e., moieties which are derived from carboxylic acids of the formula RCOOH where R is alkyl, and preferably is lower alkyl. Esters can be reconverted to the free acids, if desired, by using conventional hydrogenolysis or hydrolysis procedures. Amides and prodrugs may also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety which results in a compound that is therapeutically inactive until modified by an individual's metabolic system.

PHARMACEUTICAL FORMULATIONS AND MODES OF ADMINISTRATION:

The active agent is administered transmucosally to treat erectile dysfunction, and is accordingly administered in a pharmaceutical formulation suitable for transmucosal drug administration.

The pharmaceutical compositions may be in the form of solid, semi-solid or liquid dosage forms, such as, for example, buccal tablets, sublingual tablets, rectal suppositories, suspensions, creams, ointments, solutions, lotions, pastes or the like, preferably in unit dosage form suitable for single administration of a precise dosage. The compositions comprise an effective amount of the phosphodiesterase inhibitor in combination with a pharmaceutically acceptable carrier and, in addition, may include other pharmaceutical agents, adjuvants, diluents, buffers, etc.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington:The Science and Practice of Pharmacy, Nineteenth Ed.* (Easton, Pa.: Mack Publishing Company, 1995).

Depending on the particular phosphodiesterase inhibitor administered, it may be desirable to incorporate a permeation enhancer in the formulation in order to increase the rate at which the active agent permeates through the mucosal tissue to which it is applied, e.g., the buccal mucosa, sublingual or rectal mucosa. Examples of suitable permeation enhancers include dimethylsulfoxide ("DMSO"), dimethyl formamide ("DMF"), N,N-dimethylacetamide ("DMA"), decylmethylsulfoxide ("C$_{10}$MSO"), polyethylene glycol monolaurate ("PEGML"), glycerol monolaurate, lecithin, the 1-substituted azacycloheptan-2-ones, particularly 1-n-dodecylcyclazacycloheptan-2-one (available under the trademark Azone® from Nelson Research & Development Co., Irvine, Calif.), SEPA® (available from Macrochem Co., Lexington, Mass.), alcohols (e.g., ethanol), surfactants as discussed above, including, for example, Tergitol®, Nonoxynol-9® and TWEEN-80®, and lower alkanols such as ethanol.

The formulations may additionally include one or more enzyme inhibitors effective to inhibit drug-degrading enzymes which may be present at the site of administration. Such enzyme inhibiting compounds may be determined by those skilled in the art by reference to the pertinent literature and/or using routine experimental methods. Additional optional components include excipients, binders, fillers, lubricants (e.g., stearates such as magnesium stearate), preservatives (e.g., antioxidants), chelating agents, solubilizing agents (e.g., surfactants), and the like, as will be appreciated by those skilled in the art of drug formulation preparation and delivery.

Transmucosal drug may involve administration of any type of formulation or dosage unit suitable for application to the mucosal tissue. For example, the selected active agent may be administered in an ointment, cream, paste, or the like, or in a solid dosage form unit to be placed under the tongue (sublingual formulations), affixed to the buccal mucosa as an adhesive tablet or patch (buccal formulations), or placed within or near the rectum (transrectal formulations).

Preferred buccal dosage forms will typically comprise a therapeutically effective amount of the selected phosphodiesterase inhibitor and a biocrodible (hydrolyzable) polymeric carrier that may also serve to adhere the dosage form to the buccal mucosa. The buccal dosage unit is fabricated so as to erode gradually over a predetermined time period, wherein drug delivery is provided essentially throughout. The time period is typically in the range of approximately 0.5 hours to 24 hours. Buccal drug delivery, as will be appreciated by those skilled in the art, avoids the disadvantages encountered with oral drug administration, e.g., slow absorption, degradation of the active agent by fluids present in the gastrointestinal tract and/or first-pass inactivation in the liver. The "therapeutically effective amount" of phosphodiesterase inhibitor in the dosage unit will of course depend on the potency of the agent and the intended dosage, which, in turn, is dependent on the particular individual undergoing treatment, the specific indication, and the like. Suitable doses of specific phosphodiesterase inhibitors will be known to those skilled in the art, or may be deduced from the literature in combination with the teaching of the present disclosure. By way of example, a typical daily dosage of sildenafil citrate for treatment of sexual dysfunction as discussed herein is in the range of about 25 to 100 mg, although more or less may be effective. The dosage unit will generally contain from approximately 1.0 wt. % to about 60 wt. % active agent, preferably on the order of 1 wt. % to about 30 wt. % active agent. With regard to the bioerodible (hydrolyzable) polymeric carrier, it will be appreciated that virtually any such carrier can be used, so long as the desired drug release profile is not comprised, and the carrier is compatible with the phosphodiesterase inhibitor to be administered and any other components that may be present in the buccal dosage unit. Generally, the polymeric carrier comprises hydrophilic (water-soluble and water-swellable) polymers that adhere to the wet surface of the buccal mucosa. Examples of polymeric carriers useful herein include acrylic acid polymers and co, e.g., those known as "carbomers" (Carbopol®, which may be obtained from B.F. Goodrich, is one such polymer). Other suitable polymers include, but are not limited to: hydrolyzed polyvinylalcohol; polyethylene oxides (e.g., Sentry Polyox® water soluble resins, available from Union Carbide); polyacrylates (e.g., Gantrez®, which may be obtained from GAF); vinyl polymers and copolymers; polyvinylpyrrolidone; dextran; guar gum; pectins; starches; and cellulosic polymers such as hydroxypropyl methylcellulose, (e.g., Methocel®, which may be obtained from the Dow Chemical Company), hydroxypropyl cellulose (e.g., Klucel®, which may also be obtained from Dow), hydroxypropyl cellulose ethers (see, e.g., U.S. Pat. No. 4,704,285 to Alderman), hydroxycthyl cellulose, carboxymethyl cellulose, sodium carboxymethyl cellulose, methyl cellulose, ethyl cellulose, cellulose acetate phthalate, cellulose acetate butyrate, and the like.

Other components may also be incorporated into the buccal dosage forms described herein. The additional components include, but are not limited to, disintegrants, diluents, binders, lubricants, flavoring, colorants, preservatives, and the like. Examples of disintegrants that may be used include, but are not limited to, cross-linked polyvinylpyrrolidones, such as crospovidone (e.g., Polyplasdone® XL, which may be obtained from GAF), cross-linked carboxylic methylcelluloses, such as croscarmelose (e.g., Ac-di-sol®, which may be obtained from FMC), alginic acid, and sodium carboxymethyl starches (e.g., Explotab®, which may be obtained from Edward Medell Co., Inc.), methylcellulose, agar bentonite and alginic acid. Suitable diluents are those which are generally useful in pharmaceutical formulations prepared using compression techniques, e.g., dicalcium phosphate dihydrate (e.g., Di-Tab®, which may be obtained from Stauffer), sugars that have been processed by cocrystallization with dextrin (e.g., co-crystallized sucrose and dextrin such as Di-Pak®, which may be obtained from Amstar), lactone, calcium phosphate, cellulose, kaolin, mannitol, sodium chloride, dry starch, powdered sugar and the like. Binders, if used, are those that enhance adhesion. Examples of such binders include, but are not limited to, starch, gelatin and sugars such as sucrose, dextrose, molasses, and lactose. Particularly preferred lubricants are stearates and stearic acid, and an optimal lubricant is magnesium stearate.

Preferred sublingual dosage forms include sublingual tablets, creams, ointments and pastes. The tablet, cream, ointment or paste for sublingual delivery comprises a therapeutically effective amount of the selected phosphodiesterase inhibitor and one or more conventional nontoxic carriers suitable for sublingual drug administration. The sublingual dosage forms of the present invention can be manufactured using conventional processes. The sublingual dosage unit is fabricated to disintegrate rapidly. The time period for complete disintegration of the dosage unit is typically in the range of from about 10 seconds to about 30 minutes, and optimally is less than 5 minutes.

Other components may also be incorporated into the sublingual dosage forms described herein. The additional components include, but are not limited to binders, disintegrators, wetting agents, lubricants, and the like. Examples of binders that may be used include water, ethanol, polyvinylpyrrolidone, starch solution gelatin solution, and the like. Suitable disintegrators include dry starch, calcium carbonate, polyoxyethylene sorbitan fatty acid esters, sodium lauryl sulfate, stearic monoglyceride, lactose, and the like. Wetting agents, if used, include glycerin, starches, and the like. Particularly preferred lubricants are stearates and polyethylene glycol. Additional components that may be incorporated into sublingual dosage forms are known, or will be apparent, to those skilled in this art; for example, see *Remington: The Science and Practice of Pharmacy*, 19th edition (Mack Publishing, 1995).

Preferred transrectal dosage forms include rectal suppositories, creams, ointments, and liquid formulations (enemas). The suppository, cream, ointment or liquid formulation for transrectal delivery comprises a therapeutically effective amount of the selected phosphodiesterase inhibitor and one or more conventional nontoxic carriers suitable for transrectal drug administration. The transrectal dosage forms of the present invention can be manufactured using conventional processes. The transrectal dosage unit can be fabricated to disintegrate rapidly or over the period of several hours. The time period for complete disintegration is preferably in the range of from about 10 minutes to about 6 hours, and optimally is less than 3 hours.

Other components may also be incorporated into the transrectal dosage forms described herein. The additional components include, but are not limited to, stiffening agents, antioxidants, preservatives, and the like. Examples of stiffening agents that may be used include, for example, paraffin, white wax and yellow wax. Preferred antioxidants, if used, include sodium bisulfite and sodium metabisulfite.

Ointments, as is well known in the art of pharmaceutical formulation, are semisolid preparations that are typically based on petrolatum or other petroleum derivatives. Creams containing the selected active agent, are, as known in the art, viscous liquid or semisolid emulsions, either oil-in-water or water-in-oil. Cream bases are water-washable, and contain an oil phase, an emulsifier and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing. The ointment or cream is applied to a suitable mucosal surface.

Pastes are semisolid dosage forms in which the active agent is suspended in a suitable base. Depending on the nature of the base, pastes are divided between fatty pastes or those made from a single-phase aqueous gels. The base in a fatty paste is generally petrolatum or hydrophilic petrolatum or the like. The pastes made from single-phase aqueous gels generally incorporate carboxymethylcellulose or the like as a base. The paste is applied to a suitable mucosal surface.

Suppositories are solid dosage forms in which the active agent is carried in a suitable base. Specifically shaped for insertion into body orifices, the suppository melts, softens or dissolves resulting in effective delivery of the active agent. The suppository base can be an oleaginous base, water-soluble base, or mixture of both. The base must remain a solid at room temperature but melt, soften or dissolve at body temperature. Thus, suitable suppository bases include, for example, cocoa butter, glyceryl monostearate and polyethylene glycol. The suppository is made using conventional techniques including molding, compression, or hand rolling. The suppository is inserted into a body orifice having a suitable mucosal surface.

Enemas are liquid dosage forms in which the active agent is solubilized or suspended in a suitable liquid carrier. As will be readily apparent to those skilled in the art, the selection of the liquid carrier is dependent upon the stability and chemical reactivity of the active agent. Suitable liquid carriers for enemas include, for example, sodium chloride solution. Alternative carriers, additional components and methods of preparing enemas are known to those skilled in the art or disclosed in *Remington: The Science and Practice of Pharmacy*, referenced above.

Additional pharmacologically active agents may be delivered along with the primary active agent, i.e., the phosphodiesterase inhibitor. Vasoactive agents, particularly vasodilators, are preferred additional agents. Suitable vasoactive agents include, but are not limited to, nitrovasodilators such as: nitroglycerin; linsidomine, particularly linsidomine chlorhydrate ("SIN-1"); molsidomine; organic nitrates such as isosorbide dinitrate, erythrityl tetranitrate and amyl nitrate; sodium nitroprisside; S-nitrosothiols such as S-nitroso-N-acetyl-d,1-penicillamine ("SNAP"), S-nitroso-N-cysteine and S-nitroso-N-glutathione ("SNO-GLU"); and diazenium diolates ("NONOates") such as (Z)-1- {N-methyl-N-[6-(N-methyl-ammoniohexyl)amino] }diazen-1-ium-1,2-diolate, (Z)-1-[N-(3-ammoniopropyl)-N-(n-propyl)amino]diazen-1-ium-1,2-diolate, (Z)-1-{N-[3-aminopropyl]-N-[4-(3-aminopropylammonio)butyl] amino}diazen-1-ium-1,2-diolate and sodium (Z)-1-(N,N-diethylamino)-diazen-1-ium-1,2-diolate. Other suitable vasoactive agents include, for example, long and short acting α-blockers such as phenoxybenzamine, dibenamine, doxazosin, terazosin, phentolamine, tolazoline, prazosin, trimazosin, alfuzosin, tamsulosin and indoramin; ergot alkaloids such as ergotamine and ergotamine analogs, e.g., acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride and terguride; antihypertensive agents such as diazoxide, hydralazine and minoxidil; vasodilators such as nimodipine, pinacidil, cyclandelate and isoxsuprine; chlorpromazine; haloperidol; yohimbine; Rec15/ 2739; trazodone; naturally occurring prostaglandins such as $PGE_0$, $PGE_1$, $PGA_1$, $PGB_1$, $PGF_{1\alpha}$, 19-hydroxy-$PGA_1$, 19-hydroxy-$PGB_1$, $PGE_2$, $PGA_2$, $PGB_2$, 19-hydroxy-$PGA_2$, 19-hydroxy-$PGB_2$, $PGE_3$, $PGF_{3\alpha}$; semisynthetic or synthetic derivatives of natural prostaglandins, including carboprost tromethamine, dinoprost tromethamine, dinoprostone, lipoprost, gemeprost, metenoprost, sulprostone and tiaprost; and vasoactive intestinal peptide. Prazosin, prostaglandin $E_0$, prostaglandin $E_1$, and prostaglandin $E_2$ are particularly preferred vasoactive agents to be co-administered with the active agent.

The amount of active agent administered and the dosing regimen used, will, of course, be dependent on the particular drug selected, the age and general condition of the subject being treated, the severity of the subject's condition, and the judgment of the prescribing physician. A typical daily dose of an active agent as administered transmucosally, e.g., buccally, sublingually, or transrectally, is generally in the range of approximately 0.1 to 500 mg, with 5 mg to 100 mg representing an optional dosage range for most active agents. Depending on the half-life of the drug and the availability via the chosen route of administration, the dosing regimen can be modulated in order to achieve satisfactory therapeutic results.

KITS:

The invention also encompasses a kit for patients to carry out the present method of treating premature ejaculation using transmucosal, e.g., buccal, sublingual, and transrectal drug therapy. The kit contains the pharmaceutical formulation to be administered, a container, preferably sealed, for housing the formulation during storage and prior to use, and instructions for carrying out drug administration in an effective manner. The formulation may consist of the drug in unit dosage form. The kit may contain multiple formulations of different dosages of the same agent. The kit may also contain multiple formulations of different active agents. The instructions may be in written or pictograph form, or can be on recorded media including audio tape, video tape, or the like.

USE IN CONJUNCTION WITH VENOUS FLOW CONTROL ("VFC") DEVICE:

In an alternative embodiment of the invention, a pharmaceutical formulation containing the selected phosphodiesterase inhibitor is administered transmucosally in combination with use of a venous flow control device such as that described in U.S. Pat. No. 5,855,548 to Place for "Venous Flow Control Element for Maintaining Penile Erection," assigned to VIVUS, Inc. (Mountain View, Calif.). Preferred devices are formed from a length of flexible tubing having an integral fastening means, so as to provide for readily adjustable venous flow control when applied to the penis. The device is applied to the base of the penis prior to and during sexual intercourse, such that it effectively enhances retention of blood within the penis without substantially obstructing arterial inflow or becoming too constrictive during the erectile process. In this embodiment, a kit will include the venous flow control device in addition to the components noted above, along with instructions for using the device.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains. All patents, patent applications, and publications mentioned herein are hereby incorporated by reference in their entireties.

EXAMPLE 1

Preparation of transmucosal paste: A transmucosal formulation is prepared containing zaprinast, a Type V phosphodiesterase inhibitor. 10 g of bulk zaprinast is placed in a mortar and a pestle is used to grind the solid into a fine powder. About 10 g of a previously weighed out quantity of 100 g of ORABASE® (Colgate-Hoyt Laboratories, Norwood, Mass.) is combined with the zaprinast powder on an ointment tile. The zaprinast powder and ORABASE® are levigated together using a spatula. The remaining ORABASE® is added to the ointment tile and levigated with the previously mixed components to produce a smooth, consistent formulation. The resulting formulation is a 10% zaprinast transmucosal formulation.

This procedure can be used with various phosphodiesterase inhibitors, ointment bases and additional components, e.g., enhancers or the like.

EXAMPLE 2

Preparation of transmucosal paste: A transmucosal formulation is prepared containing sildenafil citrate, a Type V phosphodiesterase inhibitor. About 5 g of bulk sildenafil citrate is placed in a mortar and a pestle is used to grind the solid into a fine powder. About 5 g of a previously weighed out quantity of 100 g of ORABASE® is combined with the sildenafil citrate powder on an ointment tile. The sildenafil citrate powder and ORABASE® are levigated together using a spatula. The remaining ORABASE® is added to the ointment tile and levigated with the previously mixed components to produce a smooth, consistent formulation. The resulting formulation is a 5% sildenafil citrate transmucosal formulation.

EXAMPLE 3

Preparation of buccal dosage form: 10 g of zaprinast and 90 g of gelatin are mixed and pulverized in a mill. After the mixing is complete, 20 g of concentrated glycerin, 10 g of lactose and 20 g of mannitol are added and the components are mixed until uniform. 150 mg aliquot portions of the mixture are compression-molded to provide a buccal dosage unit. Each buccal unit contains 10 mg of zaprinast.

EXAMPLE 4

Preparation of a buccal dosage form: 10 g of sildenafil citrate and 90 g of gelatin are mixed and pulverized in a mill. After the mixing is complete, 20 g of concentrated glycerin, 10 g of lactose and 20 g of mannitol are added and the components are mixed until uniform. 150 mg aliquot portions of the mixture are compression-molded to provide a buccal dosage unit. Each buccal unit contains 10 mg of sildenafil citrate.

EXAMPLE 5

Preparation of a buccal dosage form: 10 g of milrinone (a Type III phosphodiesterase inhibitor) and 90 g of gelatin are mixed and pulverized in a mill. After the mixing is complete, 20 g of concentrated glycerin, 10 g of lactose and 20 g of mannitol are added and the components are mixed until uniform. 150 mg aliquot portions of the mixture are compression-molded to provide a buccal dosage unit. Each buccal unit contains 10 mg of milrinone.

EXAMPLE 6

Preparation of a buccal dosage form: 10 g of rolipram (a Type IV phosphodiesterase inhibitor) and 90 g of gelatin are mixed and pulverized in a mill. After the mixing is complete, 20 g of concentrated glycerin, 10 g of lactose and 20 g of mannitol are added and the components are mixed until uniform. 150 mg aliquot portions of the mixture are compression-molded to provide a buccal dosage unit. Each buccal unit contains 10 mg of rolipram.

EXAMPLE 7

Preparation of a sublingual tablet: 1.0 g of zaprinast, 1.0 g of mannitol, 2.0 g of microcrystalline cellulose, and 10 mg of magnesium stearate are blended in a suitable mixer and then compressed into sublingual tablets. Each sublingual tablet contains 10 mg of zaprinast.

EXAMPLE 8

Preparation of a sublingual tablet: 1.0 g of sildenafil citrate, 1.0 g of mannitol, 2.0 g of microcrystalline cellulose, and 10 mg of magnesium stearate are blended in a suitable mixer and then compressed into sublingual tablets. Each sublingual tablet contains 10 mg of sildenafil citrate.

EXAMPLE 9

Preparation of a rectal suppository: A pharmaceutical formulation containing a Type V phosphodiesterase inhibitor for transrectal administration is prepared by mixing 10 to 100 mg zaprinast with polyethylene glycol, molecular weight approximately 4000, and heating the mixture to a temperature just high enough to produce a zaprinast-polymer melt. The zaprinast-polyethyleneglycol mixture can then be poured into a mold suitable to provide a zaprinast rectal suppository, and allowed to cool. The suppository so provided is a unit dosage form suitable for transrectal administration.

EXAMPLE 10

Preparation of a rectal suppository: A pharmaceutical formulation containing an a Type V phosphodiesterase inhibitor for transrectal administration is prepared by mixing 10 to 100 mg sildenafil citrate with polyethylene glycol, molecular weight approximately 4000, and heating the mixture to a temperature just high enough to produce a sildenafil citrate-polymer melt. The sildenafil citrate-polyethyleneglycol mixture can then be poured into a mold suitable to provide a sildenafil citrate rectal suppository, and allowed to cool. The suppository so provided is a unit dosage form suitable for transrectal administration.

EXAMPLE 11

An effective phosphodiesterase-inhibiting dose may be determined using the following procedures.

Buccal administration: Patients with penile vascular insufficiency are given a single dose of 0.5 g of a phosphodiesterase inhibitor (e.g., zaprinast) transbucally in a buccal dosage form. Prior to and approximately 3 hours after administering the inhibitor, blood samples are taken and assayed for plasma phosphodiesterase activity using, for example, high-performance liquid chromatography with fluorimetric detection as described by Lee et al, *J. Chromatography* 421:237–244 (1987). This procedure is repeated at 24 hour intervals with dosage adjusted as necessary.

Sublingual administration: The same procedures described for determining an effective phosphodiesterase-inhibiting dose for buccal administration are followed except that a suitable dosage form is administered sublingually.

Transrectal administration: The same procedures described for determining an effective phosphodiesterase-inhibiting dose for buccal administration are followed expect that a suitable dosage form is administered transrectally.

EXAMPLE 12

The pharmaceutical formulations of Examples 1–10 can be used to treat erectile dysfunction in individuals in which the dysfunction is associated, for example, vascular insufficiency. Dosage may be adjusted using the methodology of Example 11. In all instances the individuals are expected to respond positively, although variations in the intensity and duration of erection may be observed depending on dose, formulation and environment. Generally, between approximately 5 and 90 minutes following drug administration, it is expected that an erection may be achieved.

What is claimed is:

1. A method for treating erectile dysfunction in a male individual, comprising transmucosally administering to the individual an effective amount of a phosphodiesterase inhibitor or a pharmaceutically acceptable salt, ester, amide or prodrug thereof, wherein the phosphodiesterase inhibitor is selected from the group consisting of Type III phosphodiesterase inhibitors, Type IV phosphodiesterase inhibitors, and combinations thereof.

2. The method of claim 1, wherein administration is transbuccal.

3. The method of claim 1, wherein administration is sublingual.

4. The method of claim 1, wherein administration is transrectal.

5. The method of claim 1, wherein the phosphodiesterase inhibitor is a Type III phosphodiesterase inhibitor.

6. The method of claim 5, wherein the Type III phosphodiesterase inhibitor is selected from the group consisting of bipyridines, imidazolones, imidazolines, dihydropyridazinones, dihydroquinolones, mixed Type III–Type IV inhibitors, anagrelide, bemoradan, ibudilast, isomazole, lixazinone, motapizone, olprinone, phthalazinol, pimobendan, quazinone, siguazodan and trequinsin.

7. The method of claim 6, wherein the Type III phosphodiesterase inhibitor is a bipyridine.

8. The method of claim 7, wherein the bipyridine is selected from the group consisting of amrinone and milrinone.

9. The method of claim 5, wherein the Type III phosphodiesterase inhibitor is an imidazolone.

10. The method of claim 9, wherein the imidazolone is selected from the group consisting of piroximone and enoximone.

11. The method of claim 5, wherein the Type III phosphodiesterase inhibitor is a dihydroquinolinone.

12. The method of claim 11, wherein the dihydroquinolinone is selected from the group consisting of cilostamide, cilostazol, vesnarinone and OPC 3911.

13. The method of claim 1, wherein the phosphodiesterase inhibitor is a Type IV phosphodiesterase inhibitor.

14. The method of claim 13, wherein the Type IV phosphodiesterase inhibitor is selected from the group consisting of pyrrolidinones, quinazolinediones, xanthine derivatives, phenyl ethyl pyridines, tetrahydropyrimidones, diazepine derivatives, oxime carbamates, naphthyridinones, benzofurans, naphthalene derivatives, purine derivatives, imidazolidinones, cyclohexane carboxylic acids, benzamides, pyridopyridazinones, benzothiophenes, etazolate, S-(+)-glaucine, substituted phenyl compounds and substituted biphenyl compounds.

15. The method of claim 14, wherein the Type IV phosphodiesterase inhibitor is a pyrrolidinone.

16. The method of claim 15, wherein the pyrrolidinone is selected from the group consisting of rolipram, RO20-1724 and RS 33793.

17. The method of claim 16, wherein the pyrrolidinone is rolipram.

18. A method for treating erectile dysfunction in a male individual, comprising sublingually administering to the individual a sublingual dosage form that completely disintegrates within approximately 10 seconds to 30 minutes after administration and is selected from the group consisting of a sublingual tablet, cream, ointment or paste, said sublingual dosage form containing a therapeutically effective unit dose of an active agent selected from Type V phosphodiesterase inhibitors and pharmaceutically acceptable salts, esters, amides and prodrugs thereof, and a pharmaceutically acceptable carrier.

19. The method of claim 18, wherein the sublingual dosage form completely disintegrates in less than five minutes after administration.

20. The method of claim 18, wherein the sublingual dosage form contains at least one additional component selected from the group consisting of binders, disintegrators, wetting agents, and lubricants.

21. The method of claim 18, wherein the active agent is a pyrazolopyrimidinone or an acid addition salt thereof.

22. The method of claim 21, wherein the active agent is selected from the group consisting of zaprinast, sildenafil and sildenafil citrate.

23. A method for treating erectile dysfunction in a male individual, comprising applying to the buccal mucosa of the individual a bioerodible buccal dosage unit that adheres to the buccal mucosa and erodes thereon over a period of approximately 0.5 to 24 hours, said dosage unit containing (a) a therapeutically effective unit dose of an active agent selected from Type V phosphodiesterase inhibitors and pharmaceutically acceptable salts, esters, amides and pro-drugs thereof, and (b) a hydrolyzable polymeric carrier, wherein the active agent represents approximately 1 wt.% to 60 wt.% of the buccal dosage unit.

24. The method of claim 23, wherein the active agent represents approximately 1 wt.% to 30 wt.% of the buccal dosage unit.

25. The method of claim 23, wherein the buccal dosage unit contains at least one additional component selected from the group consisting of disintegrants, diluents, binders, lubricants, flavoring, colorants, and preservatives.

26. The method of claim 23, wherein the active agent is pyrazolopyrimidinone or an acid addition salt thereof.

27. The method of claim 26, wherein the active agent is selected from the group consisting of zaprinast, sildenafil, and sildenafil citrate.

28. The method of claim 27, wherein the active agent is sildenafile citrate.

29. The method of claim 28, wherein the therapeutically effective unit dose is in the range of about 25 mg to 100 mg.

30. A method for treating erectile dysfunction in a male individual, comprising transrectally administering to the individual a transrectal dosage form that completely disintegrates within approximately 10 minutes to 6 hours following administration and is selected from the group consisting of a rectal suppository, cream, ointment, and enema solution, said transrectal dosage form containing a therapeutically effective amount unit dose of an active agent selected from Type V phosphodiesterase inhibitors and pharmaceutically acceptable salts, esters, amides and prodrugs thereof, and a pharmaceutically acceptable carrier.

31. The method of claim 30, wherein the transrectal dosage form completely disintegrates within approximately 3 hours following administration.

32. The method of claim 30, wherein the transrectal dosage form is a rectal suppository.

33. The method of claim 32, wherein the rectal suppository further includes at least one additional component selected from the group consisting of stiffening agents, antioxidants, and preservatives.

34. The method of claim 30, wherein the active agent is pyrazolopyrimidinone or an acid addition salt thereof.

35. The method of claim 34, wherein the active agent is selected from the group consisting of zaprinast, sildenafil, and sildenafile citrate.

36. The method of claim 33, wherein the daily dose is in the range of 5 to 100 mg.

37. The method of any one of claims 18, 23 or 30, wherein the Type V phosphodiesterase inhibitor is selected from the group consisting of zaprinast; dipyridamole; pyrazolopyrimidinones; griseolic acid derivatives; 2-phenylpurinones; phenylpyridone derivatives; pyrimidines; pyrimidopyrimidines; purines; quinazolines; phenylpyrimidinones; imidazoquinoxalinones or aza analogues thereof; phenylpyridones; 4-bromo-5-(pyridylmethylamino)-6-[3-(4-chlorophenyl)propoxy]-3(2H)pyridazinone; 1-[4-[(1,3-benzodioxol-5-ylmethyl)amiono]-6-chloro-2-quinazolinyl]-4-piperidine-carboxylic acid, monosodium salt; (+)-cis-5,6a,7,9,9,9a-hexahydro-2-[4-(trifluoromethyl)-phenylmethyl-5-methyl-cyclopent-4,5]imidazo[2,1-b]purin-4(3H)one; furazlocillin; cis-2-hexyl-5-methyl-3,4,5,6a,7,8,9,9a-octahydrocyclopent[4,5]imidazo[2,1-b]purin-4-one; 3-acetyl-1-(2-chlorobenzyl)-2-propylindole-6-carboxylate; 4-bromo-5-(3-pyridylmethylamino)-6-(3-(4-chlorophenyl) propoxy)-3-(2H)pyridazinone; 1-methyl-5-(5-morpholinoacetyl-2-n-propoxyphenyl)-3-n-propyl-1,6-dihydro-7H-pyrazolo(4,3-d)pyrimidin-7-one; 1-[4-[(1,3-benzodioxol-5-ylmethyl)amino]-6-chloro-2-quinazolinyl]-4-piperidinecarboxylic acid, monosodium salt; pyrrolo[1,2-c]imidazolone derivatives; 1-phenylmethyl-N-[[4-ethyl-2-(2-ethyl-4-methyl-1H-imidazol-1-yl)]pyrimidin-5-yl]-1H-imidazol-2-carboxamide; 1-phenylmethyl-N-[4-ethyl-2-(1H-imidazol-1-yl)pyrimidin-5-yl]-1H-imidazol-2-carboxamide; 4,9-diethyl-2-(2-ethyl-4-methyl-1H-imidazol-1-yl)-7-methylimidazo[5,1-h]pteridin-6(5H)-one; and 9-ethyl-2(2-ethyl-4-methyl-1H-imidazol-1-yl)-7-methyl-4-(2-propyl)imidazo[5,1-h]pteridin-6(5H)-one.

38. The method of claim 37, wherein the Type V phosphodiesterase inhibitor is zaprinast.

39. The method of claim 37, wherein the Type V phosphodiesterase inhibitor is a pyrazolopyrimidinone.

40. The method of claim 39, wherein the Type V phosphodiesterase inhibitor is sildenafil or a pharmaceutically acceptable salt thereof.

41. The method of claim 1, wherein the phosphodiesterase inhibitor is selected from the group consisting of pentoxifylline, doxazosin, papaverine, prazosin, terazosin, trimazosin and hydralazine.

42. The method of any one of claims 1, 18, 23 and 30, wherein the individual is given a daily dose of phosphodiesterase inhibitor in the range of approximately 0.1 to 500 mg.

43. The method of any one of claims 1, 18, 23 and 30, wherein the phosphodiesterase inhibitor is administered one to four times in a twenty-four hour period.

44. The method of any one of claims 1, 18, 23 and 30, wherein the erectile dysfunction is vasculogenic impotence.

45. The method of any one of claims 1, 18, 23 and 30, wherein the phosphodiesterase inhibitor is contained within a pharmaceutical formulation comprising an additional active agent.

46. The method of claim 45, wherein the additional active agent is a vasoactive agent.

47. The method of claim 45, wherein the additional active agent is a smooth muscle relaxant.

48. The method of any one of claims 1, 18, 23 and 30, wherein the phosphodiesterase inhibitor is contained within a unit dosage pharmaceutical formulation.

49. The method of claim 18, wherein the active agent is tadalafil.

50. The method of claim 23, wherein the active agent is tadalafil.

51. The method of claim 30, wherein the active agent is tadalafil.

* * * * *